US00PP14154P39

(12) United States Plant Patent
May

(10) Patent No.: US PP14,154 P3
(45) Date of Patent: Sep. 23, 2003

(54) CHRYSANTHEMUM PLANT NAMED 'JMAY01'

(76) Inventor: James D. May, 114 Fel Mar Dr., San Luis Obispo, CA (US) 93405

( * ) Notice: Subject to any disclaimer, the term of this patent is extended or adjusted under 35 U.S.C. 154(b) by 0 days.

(21) Appl. No.: 10/055,860

(22) Filed: Jan. 22, 2002

(65) Prior Publication Data

US 2003/0140389 P1 Jul. 24, 2003

(51) Int. Cl.[7] ..... A01H 5/00
(52) U.S. Cl. ..... Plt./287
(58) Field of Search ..... Plt./287, 288, 289

(56) References Cited

U.S. PATENT DOCUMENTS

PP4,476 P 11/1979 Petusky ..... Plt./289

*Primary Examiner*—Bruce R. Campell
*Assistant Examiner*—June Hwu

(57) ABSTRACT

A new and distinct Chrysanthemum plant cultivar characterized by solitary, decorative flowers having a bright golden yellow coloration of the inner ray petals, gradually turning to a white coloration towards the outer ray petals, blooming consistently after 56 days of a 12/12 daylight/darkness cycle, having a free branching habit, and a consistent natural season flowering habit during the fall.

1 Drawing Sheet

Latin name of the genus and species claimed: *Chrysanthemum×morifolium.*
Variety denomination: 'JMay01'.

BACKGROUND OF THE INVENTION

The present invention relates to a new and distinct cultivar of Chrysanthemum plant, herein after referred to by the cultivar name 'JMay01'. The new cultivar is a two tone natural mutation of the variety 'Casper' (unpatented) discovered in a controlled greenhouse environment in San Luis Obispo, Calif.

Asexual reproduction of the new cultivar by apical tip cutting and meristem tissue culture was performed in San Luis Obispo, Calif., and has shown that the unique features of this new Chrysanthemum cultivar are stable and reproduce true to type on successive generations.

SUMMARY OF THE INVENTION

The cultivar 'JMay01' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'JMay01'. The new cultivar 'JMay01' naturally blooms in the fall season. The 10–12 cm solitary, decorative inflorescences have bright golden yellow inner ray petals of about 4.6 cm, which radiate out to light, almost white outer ray florets. Floral bloom occurs after about 56 days of a 12 hour light/12 hour darkness cycle. The color of the petals change as the flower ages: the outer ray florets fade to white with age, while the inner petals fade to a golden yellow with age. No seeds are produced. The plant is perennial, herbaceous, and has excellent disease resistance characteristics. The new cultivar 'JMay01' has a free branching semi-upright habit, growing to about 25–35 cm as a disbud pot mum. The fragrance of the herbage is strong and pungent, while the inflorescence has little to no fragrance. The mature leaves are about 8–10 cm in length by 6–8 cm in width, and have a lanceolate shape with an acute apex.

The new cultivar 'JMay01' can be distinguished as a new and distinct Chrysanthemum cultivar by its bright golden yellow coloration of inner ray floret radiating out to white outer ray floret.

Plants of the new cultivar are similar to plants of the parent cultivar, 'Casper' in most horticultural characteristics, differing from the parent cultivar 'Casper' primarily in bloom characteristics. Plants of the new cultivar can be distinguished from its parent cultivar 'Casper' by the bright golden yellow coloration of its inner ray florets and white coloration of its outer ray florets. The parent cultivar 'Casper', in contrast, has pale yellow inner ray florets.

Plants of the new cultivar are similar to the cultivar 'Sunburst Spirit' (U.S. Plant Pat. No. 4,476). The new cultivar can be distinguished from the cultivar 'Sunburst Spirit' by having a bright golden yellow coloration of its inner ray florets, as compared to the light yellow coloring of the inner ray florets of the 'Sunburst Spirit' cultivar.

BRIEF DESCRIPTION OF THE PHOTOGRAPH

The photograph shows a plant of the new cultivar which was grown in a 6½-inch container. Five cuttings were grown in the container, and the plant was grown under greenhouse conditions.

DETAILED BOTANICAL DESCRIPTION

In the following description, color references are made to The Royal Horticultural Society Colour Chart except where general terms of ordinary dictionary significance are used. The following observations and measurements describe 10 week old plants grown in a greenhouse in San Luis Obispo, Calif., in the month of September 2000. The growing conditions range from 60° to 65° F. at night to 70° to 85° F. during the day. Measurements and numerical values represent averages of typical flowering types.

Botanical classification: *Dendranthema grandiflora* cultivar 'JMay01'.

Commercial classification: Florist Chrysanthemum.
Parentage: Natural mutation of the variety 'Casper' discovered in a controlled greenhouse environment.

PROPAGATION

Time to rooting: 3 to 5 days.
Rooting habit: Basal swelling, callusing, and profuse root production just above base of cutting.

PLANT

Growth habit: Semi-upright.
Plant spread: Approximately 15 inches.
Height: 25–35 cm as a disbud pot mum with 0–7 long days after pinch, but prior to short days and 2 applications of 2500 ppm B-9 sp.
Growth rate: 2–3 cm per week after pinch.
Branching characteristics: Free branching.

FOLIAGE

Leaf:
*Arrangement.*—Alternate.
*Average length.*—Approximately 8–10 cm.
*Average width.*—Approximately 6–8 cm.
*Shape of blade.*—Lanceolate.
*Apex.*—Acute.
*Base.*—Attenuate.
*Attachment.*—Attenuate to stem.
*Margin.*—Moderately to deeply lobed and slightly serrate.
*Texture of top surface.*—Canescent.
*Texture of bottom surface.*—Pubescent.
*Color.*—Young foliage upper side: Near yellow-green 147A. Young foliage under side: Near green 137B. Mature foliage upper side: Near green 139A. Mature foliage under side: Near green 137B. Venation upper side: Near green 138C. venation under side: Near green 138B.
Petiole:
*Average length.*—Attenuate to stem — no pronounced petiole.

BLOOM

Inflorescence:
*Flowering habit.*—Requires about 12 hours light/12 hours darkness for approximately 56 days to induce and develop blooms.
*Inflorescence form.*—Solitary.
*Bloom type.*—Quilled.
*Natural flowering season.*—Fall.
*Number of inflorescences per stem.*—One.
*Inflorescence diameter.*—About 10–12 cm.
*Inflorescence depth.*—About 2–3 cm.
*Inflorescence longevity on plant.*—Approximately 21–28 days.
*Persistence.*—Persistent.
Ray florets:
*Appearance.*—Matte.
*Texture.*—Glabrous.
*Average number per flower.*—Approximately 150–200.
*Shape.*—Oblanceolate.
*Margin.*—Entire.
*Tip/apex.*—Obtuse to retuse.
*Base.*—Tapered.
*Aspect.*—Straight.
*Length.*—Approximately 4.6 cm.
*Width.*—Approximately 1.0 cm.
*Color.*—Upper surface at first opening: Inner ray florets: Near yellow 9B. Outer ray florets: Near white 155A to near yellow 4D. Upper surface at maturity: Inner ray florets: Near yellow 8B. Outer ray florets: Near white 155A to near yellow 4D. Upper surface at fading: Inner ray florets: Near yellow 4C. Outer ray florets: Near white 155A to near yellow 4D. Under surface at first opening: Inner ray florets: Near yellow 9B. Outer ray florets: Near white 155A to near yellow 4D. Under surface at maturity: Inner ray florets: Near yellow 8B. Outer ray florets: Near white 155A to near yellow 4D. Under surface at fading: Inner ray florets: Near yellow 4C. Outer ray florets: Near white 155A to near yellow 4D.
Disc florets:
*Number per flower.*—Approximately 10–12.
*Color.*—Near Yellow 9B.
*Length.*—Approximately 10–12 mm.
*Width.*—Approximately 2 mm.
*Apex.*—Slightly dentate.
Peduncle:
*Length.*—Approximately 0.8–1.2 cm.
*Strength.*—Strong.
*Color.*—Near green 138C.
*Habit.*—Erect.
*Surface.*—Pubescent.
Inflorescence bud:
*Length.*—Approximately 0.8–1.0 cm.
*Diameter.*—Approximately 1.2–1.4 cm.
*Form.*—Globular.
*Color.*—Near green 141B.
Phyllaries:
*Length.*—Approximately 10–12 mm.
*Width.*—Approximately 3–5 mm.
*Appearance.*—*Matte.*
*Texture.*—Pubescent.
*Number.*—Numerous — first set of phyllaries, then a single layer of ray florets followed by a second layer of several phyllaries thick, followed by inner petals.
*Shape.*—Ovate.
*Margin.*—Entire.
*Apex.*—Acute.
*Color.*—Upper side: Near green 131A. Under side: Near green 139A.

REPRODUCTIVE ORGANS

Reproductive organs of the ray florets:
*Number of pistils per flower.*—1.
*Stigma shape.*—Linear.
*Stigma color.*—Near yellow-orange 17A.
*Style color.*—Near yellow-orange 17A.
*Style length.*—About 3–5 mm.
*Stamens.*—Absent.
Reproductive organs of the disc florets:
*Number of pistils per flower.*—1.
*Stigma shape.*—Linear.
*Style length.*—3–5 mm.
*Number of stamens per flower.*—5.
*Anther shape.*—Syngenesious.
*Anther color.*—Near yellow 8A at top, fading to near yellow 8D at base.
*Pollen color.*—Near yellow-orange 17A.
*Pollen quantity.*—Low.

OTHER CHARACTERISTICS

Seed production: None.

Disease resistance: Neither resistance nor susceptibility to diseases and pests has been observed in this cultivar to date.

Plant hardiness: This cultivar has been grown under controlled conditions in a greenhouse. Therefore, neither cold resistance nor heat resistance has been observed in this cultivar to date.

What is claimed is:

1. A new and distinct cultivar of Chrysanthemum plant named 'JMay01' as herein illustrated and described.

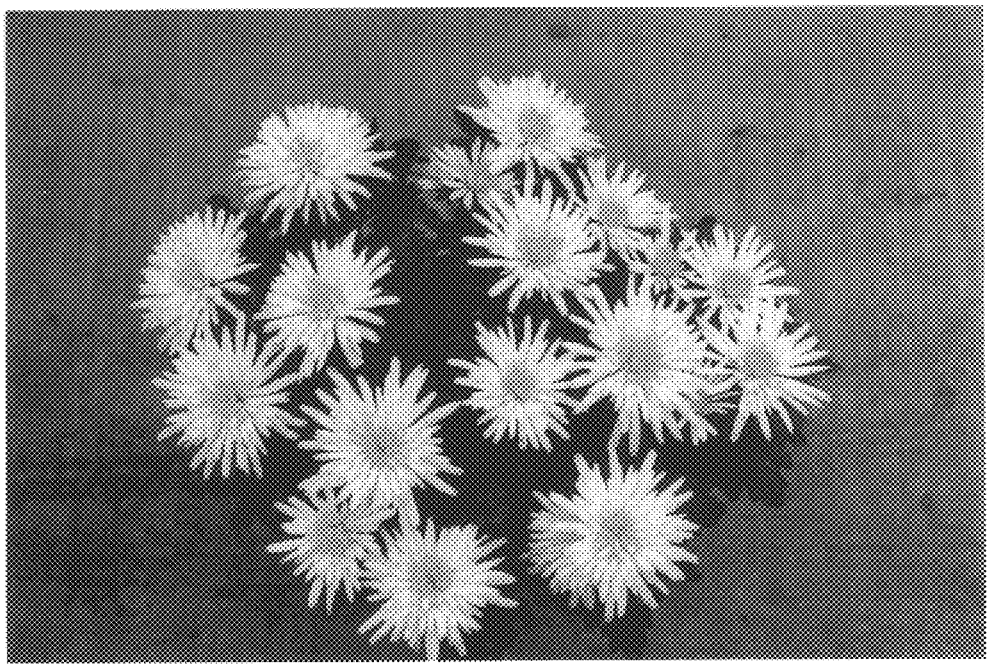

* * * * *